(12) United States Patent
Sabetsky

(10) Patent No.: US 7,781,400 B2
(45) Date of Patent: Aug. 24, 2010

(54) PHARMACEUTICAL COMPOSITIONS COMPRISING DEXTRAN WITH A MOLECULAR WEIGHT OF 1.0-100 KDA AND PROCESSES FOR THEIR PREPARATION

(75) Inventor: Vladimir A. Sabetsky, Stockholm (SE)

(73) Assignee: BOWS Pharmaceuticals AG, Zug (CH)

( * ) Notice: Subject to any disclaimer, the term of this patent is extended or adjusted under 35 U.S.C. 154(b) by 0 days.

(21) Appl. No.: 12/510,533

(22) Filed: Jul. 28, 2009

(65) Prior Publication Data

US 2009/0281020 A1 Nov. 12, 2009

Related U.S. Application Data

(63) Continuation of application No. 12/161,324, filed as application No. PCT/SE2007/050027 on Jan. 17, 2007.

(30) Foreign Application Priority Data

Jan. 18, 2006 (SE) .................... 0600091

(51) Int. Cl.
*A61K 38/28* (2006.01)
*A61K 38/02* (2006.01)
*A61K 9/16* (2006.01)
*A61K 9/50* (2006.01)
*A61K 9/52* (2006.01)

(52) U.S. Cl. .......... 514/3; 514/2; 514/59; 424/400; 424/493; 524/54; 436/529

(58) Field of Classification Search .............. None
See application file for complete search history.

(56) References Cited

U.S. PATENT DOCUMENTS

| 4,713,249 | A | 12/1987 | Schröder |
| 7,008,643 | B1 | 3/2006 | Hilgers |
| 2001/0007665 | A1 | 7/2001 | Illum et al. |
| 2003/0026844 | A1 | 2/2003 | Lee et al. |
| 2004/0234615 | A1 | 11/2004 | Sabetsky |
| 2004/0234616 | A1 | 11/2004 | Sabetsky |

FOREIGN PATENT DOCUMENTS

| EP | 1 184 032 A1 | 3/2002 |
| WO | WO 84/00294 A1 | 2/1984 |
| WO | WO 87/02704 A1 | 5/1987 |
| WO | WO 98/14174 A1 | 4/1998 |
| WO | WO 01/03667 A1 | 1/2001 |
| WO | WO 02/17884 A1 | 3/2002 |
| WO | WO 03/024425 A1 | 3/2003 |
| WO | WO 2005/102285 A1 | 11/2005 |

OTHER PUBLICATIONS

Stenekes, R.J., et al., "Formation of dextran hydrogels by crystallization," *Biomaterials* 22:1891-1898, Butterworth-Heinemann (2001).

Schröder, U., "Crystallized Carbohydrate Spheres for Slow Release and Targeting," *Methods Enzymol.* 112:116-128, Academic Press (1985).

Schröder, U., "Crystallized carbohydrate spheres as a slow release matrix for biologically active substances," *Biomaterials* 5:100-104, Butterworth-Heinemann (1984).

Moriyama, K., and Yui, N., "Regulated insulin release from biodegradable dextran hydrogels containing poly(ethylene glycol)," *J. Controlled Rel.* 42:237-248, Elsevier Science Publishers (1996).

*Primary Examiner*—Julie Ha
(74) *Attorney, Agent, or Firm*—Sterne, Kessler, Goldstein & Fox P.L.L.C.

(57) ABSTRACT

A solid or semisolid implant obtainable by providing a liquid composition comprising an aqueous solution of dextran with molecular weight of 1.0-100 kDa and introducing the liquid composition into the body of a mammal, whereby the implant is formed in situ in the body of the mammal. A process for preparing a composition useful for biomedical application, comprising the steps of providing a liquid composition comprising an aqueous solution of dextran having a molecular weight of 1-100 kDa; and bringing the liquid composition to solidify; whereby water is gradually eliminated from the liquid composition during the solidification. A biomedical article prepared from the composition.

16 Claims, 2 Drawing Sheets

US 7,781,400 B2

PHARMACEUTICAL COMPOSITIONS COMPRISING DEXTRAN WITH A MOLECULAR WEIGHT OF 1.0-100 KDA AND PROCESSES FOR THEIR PREPARATION

CROSS-REFERENCE TO RELATED APPLICATIONS

The present application is a continuation of U.S. application Ser. No. 12/161,324, filed Jul. 17, 2008, which is the 35 U.S.C. §371 U.S. national phase filing of International Application No. PCT/SE2007/050027, filed on Jan. 17, 2007, which was published in the English language on Jul. 26, 2007, as WO 2007/084068, and which claims priority to Swedish Patent Application No. SE 0600091-3, filed on Jan. 18, 2006, the contents of all of which are incorporated herein by reference in their entireties.

FIELD OF THE INVENTION

The present invention generally relates to new dextran matrices and to methods for preparing them. Furthermore, the invention relates to articles and compositions based on said matrices and to the use of these articles and compositions for biomedical applications.

BACKGROUND

Compared to development of new drugs, drug delivery products often demand less development time and costs, especially when the active ingredient has been previously well characterized for safety and toxicity. In addition, drug delivery technologies can be used for new chemical entities (NCE), enabling them to be formulated in spite of challenging pharmaceutical properties. (M. V. Chaubal, "Application of Drug Delivery Technologies in Lead Candidate Selection and Optimization", Drug Discovery Today, 9, (14), 603-609, 2004).

Controlled release and targeted delivery of drugs are two major concepts the drug delivery technologies are based on. Successful realization of these concepts can reduce side effects, improve bioavailability and stability of many drugs as well as enhance patient compliance and prevent medication errors.

The oral route is the most convenient method of drug administration and even small improvements in oral drug delivery technology may enhance patient compliance and drug bioavailability. The current drug delivery technologies are mainly focused on delayed release, i.e., no release until the dosage form reaches the specific region of GIT such as upper intestine or colon. For example, site specific delivery into the upper intestine has been achieved for many years by the use of pH-sensitive coatings.

Gelatin capsules are most popular for oral drug delivery, but the physicochemical properties of the gelatin capsule shell present significant challenges when these capsules are being coated with enteric polymers. HPMC capsules have some advantages compared to gelatin ones and U.S. Pat. No. 7,094,425 provides HPMC capsule with a suitable coating such that the drug is released from the capsule either in the small intestine or the colon.

However, there still remains an urgent need for new materials allowing further progress in the area Injectable in situ forming devices (ISFDs) based on biodegradable biocompatible polymers are very attractive as controlled release drug delivery systems. They are potentially compatible with all types of tissues and drugs, offer systemic or local drug delivery, easy to administer, simple and inexpensive to produce.

Similar to injectable drug delivery systems based on microspheres, ISFDs avoid the incision needed to implant drug delivery systems. However, the manufacture and storage of microspheres present a lot of problems. Also, once implanted in the body, due to their particulate nature, the microspheres tend to aggregate and migrate, which makes their behaviour hard to predict. Further, if there are some complications, removal of microspheres from the body without extensive surgical intervention is considerably more difficult or impossible.

At present, proteins and peptides are becoming common drugs and a lot of recombinant proteins are in clinical trials or have already received approval of regulatory authorities. In current treatments, frequent injections or infusion therapy are the prescribed dosing regimes for most of them and due to the short plasma half-life and instability of proteins, there are urgent needs for suitable delivery systems. ISFDs are theoretically excellent delivery systems for such type of drugs.

Despite intense efforts aimed at developing the technology in order to avoid the problem of protein instability during the production of ISFD, progress within this field has been very slow, the main reason probably being that the three-dimensional structure for the majority of proteins is far too sensitive to withstand the manufacturing conditions used. For example, the scientific literature contains numerous descriptions of stability problems in the manufacture of implants based on degrading poly(lactic-co-glycolic acid) (PLGA) owing to exposure to organic solvents and the acidic environment which is formed upon the degradation of PLGA matrices. It has recently been shown that the pH value in a PLGA microsphere falls to 1.5, which is fully sufficient to denature or damage many therapeutically usable proteins (Fu et al, Visual Evidence of Acidic Environment Within Degrading Poly(lactic-co-glycolic acid) (PLGA) Microspheres, Pharmaceutical Research, Vol. 17, No. 1, 2000, 100-106). For PLGA implants the pH value can be expected to fall further owing to the fact that the acidic degradation products then get more hindered from diffusing away and the autocatalytic reaction of degradation is intensified. The nature of PLGA biodegradation is such that the degradation products formed are able to catalyze further hydrolysis, by virtue of their acid groups, and this leads to an intensive biodegradation and high rate of biodegradation, and consequently a substantial reduction of the pH inside the microparticles, some weeks, or months, after injection of the formulation.

A number of attempts to solve the above-described problems caused by exposure of the biologically active substance to a chemically acidic environment during the biodegradation of the PLGA matrix and organic solvents in the manufacturing process have been described. Attempts have been made to replace PLGA as the matrix by polymers that produce chemically neutral degradation products, e.g., amino acids and PEG (US Patent Application 20040077780).

Some excellent reviews on ISFD are:

"New biodegradable polymers for injectable drug delivery systems" (B. Jeong, Y. K. Choi, Y. H. Bae, G. Zentner, S. W. Kim, Journal of Controlled Release 62 (1999) 109-114)

"In situ forming parenteral drug delivery systems: an overview" (C. B. Packhaeuser, J. Schnieders, C. G. Oster, T. Kissel, European Journal of Pharmaceutics and Biopharmaceutics 58 (2004) 445-455), "In situ-forming hydrogels—review of temperature-sensitive systems. Review article" (Eve Ruel-Gariepy, Jean-Christophe Leroux, European Journal of Pharmaceutics and Biopharmaceutics 58 (2004) 409-426).

In situ gelation of injectable systems can be based on change in molecular association of specific polymers driven by changes in temperature, pH, ion or solvent composition. Many polymers, which can be potentially used for ISFD, are new chemical entities (NCE) and not suitable for parenteral administrations, especially repeated parenteral administration, for a number of reasons. The most important of all is low biocompatibility of polymer matrices with mammal's tissues.

From the above, it appears that there is an emerging need for biodegradable and biocompatible materials that gel in situ and that may be used in a process for the production of ISFD for controlled, sustained or delayed release of biologically active substances.

Such biodegradable and biocompatible materials should be such as to permit the biologically active substances to be entrapped under conditions which allow them to retain their biological activity, in a process which permits high loading of a parenterally administrable preparation even with sensitive, biologically active substances.

The biodegradable and biocompatible materials should also be such as to allow a substantially fully biodegradable and biocompatible preparation to be produced and applied.

SUMMARY OF THE INVENTION

One object of the invention is to provide biocompatible, biodegradable polymer matrices for ISFD, capable of containing biologically active substances such that the bioactivity of said substances is essentially maintained during the manufacturing process as well as after administration.

Another object of the invention is to provide matrices for capsules aimed to targeted delivery into specific sites of GIT.

A still further object of the invention is to provide methods and compositions useful for injectable controlled release depot systems, bulking agents for soft tissue augmentation, and many types of medical devices.

Thus, in one embodiment of the invention, a solid or semi-solid implant is provided, by preparing a liquid composition comprising an aqueous solution of dextran with molecular weight of 1.0-100 kDa and introducing the liquid composition into the body of a mammal, whereby the implant is formed in situ in the body of the mammal.

In another embodiment of the invention, a process for preparing an implant is provided, comprising preparing a liquid composition comprising an aqueous solution of dextran with molecular weight of 1.0-100 kDa, optionally mixing this liquid composition with a biologically active substance, and injecting the liquid composition into the body of a mammal, whereby it solidifies in the body to form a (semi)solid implant. A method of treatment of a mammal in need of an implant is further provided by use of the above-mentioned process.

The term "semisolid implant" as used according to the present invention refers to an implant having a rigidity and viscosity intermediate between a solid and a liquid.

In one embodiment, dextran is present in the liquid composition at a concentration within the range of 50-75% wt, preferably 60-70% wt.

In one embodiment of the implant, the molecular weight of dextran may range from 1 kDa up to 100 kDa, e.g. from 1 to 70 kDa.

The liquid composition used in preparing the implant preferably is sterile and pyrogen free.

Very advantageously, the implant of the present invention is an in situ forming device (ISFD) and as such it may be formed in the body of a mammal by introducing the liquid composition comprising the dextran solution and optionally any biologically active substance. The introduction may be made e.g. by infusion or by means of a hypodermic syringe, e.g. by means of a 25-gauge or finer needle, e.g. a 22-gauge needle.

In one embodiment, the liquid composition further comprises a biologically active substance, dissolved or suspended therein. The biologically active substance suitably may be present in the liquid composition in a concentration of from 0.01 to 25% by weight.

In one embodiment, it is contemplated that the implant may contain more than one biologically active substance.

In one embodiment, if the implant is to be used for soft tissue augmentation, it is contemplated that no biologically active substance is present in the liquid composition.

The biologically active substance may be added to the liquid composition e.g. as a particulate powder or as a solution in a solvent compatible with the aqueous solution of dextran. It may be incorporated into the water used for dissolving dextran before adding dextran.

For the purpose of the present invention, and unless otherwise indicated, the term "biologically active substance" refers to a substance having a desired biological activity or effect when administered to a mammal subject. It is contemplated that it may be selected from e.g. proteins, polypeptides, peptides, organic molecules, oligo- or polynucleotides, or any other biologically active molecules. For example, the biologically active substance may be selected from growth factors, insulin, erythropoietin, interferon alpha, interferon beta, interferon gamma, blood coagulation factors V-XIII, protein C, glucagon-like peptide 1 or 2, C-peptide, vaccines, hormones, e.g. sex hormones, epidermal growth hormone, human growth hormone, LHRH-analogues, macrophage colony-stimulating factor, granulocyte colony-stimulating factor, leptin, interleukin, zinc finger nuclease or an analogue or derivative of any one thereof, and organic molecules (e.g., steroids, analgesics, local anesthetics, antibiotic agents, chemotherapeutic agents, immunosuppressive agents, anti-inflammatory agents, antiproliferative agents, antimitotic agents, angiogenic agents, anticoagulants), oligo- or polynucleotides (e.g., oligo-nucleotides for homologous recombination, plasmids containing genes encoding the proteins, polypeptides, peptides, siRNA), and any other biologically active molecule.

In one embodiment of the invention, the liquid composition for forming the implant is freeze-dried, using freeze-drying technology as well-known to the person skilled in the art. The freeze-dried composition may then be conveniently stored until use, when it is rehydrated to the initial water concentration before introducing it into the body of a mammal.

In another embodiment of the invention a process for preparing a composition useful for biomedical application is provided, comprising the steps of (a) providing a liquid composition comprising an aqueous solution of dextran having a molecular weight of 1-100 kDa; and (b) bringing the liquid composition to solidify;

wherein water is gradually eliminated from the liquid composition during step (b).

In one embodiment of the inventive process, the molecular weight of dextran may range from 1 kDa to 100 kDa, e.g. from 1 kDa to 70 kDa.

In one embodiment of the process, it is contemplated that dextran may be present in the liquid composition at an initial concentration within the range of 25-75% wt, e.g. at a concentration range of 50-75% wt.

The process of the present invention for preparing a biomedical device, comprises eliminating water from the liquid composition and this may be performed e.g. e.g. by evaporation of water or by extraction of water.

The evaporation may be performed at temperature of from 0 to 100° C., e.g. from 0 to 50° C., such as a temperature of from 10 to 40° C., e.g. from 20 to 37° C.

The rate of evaporation suitably is from 0.1 to 75, e.g. from 1 to 50, or from 5 to 20% by weight of the liquid composition of step (a) per hour.

In one embodiment, in step (b), water is eliminated from the liquid composition by extraction, by adding 1-10 parts by weight of ethanol, liquid polyethylene glycol (PEG), or liquid polypropylene glycol (PPG) to 1 part by weight of the liquid composition of step (a).

In one embodiment of the process for preparing a composition useful for biomedical application, the liquid composition further comprises a biologically active substance, as defined herein above, which may be present as a solution or dispersion (suspension or emulsion).

The biologically active substance suitably may be present in the liquid composition in a concentration of from 0.01 to 25% by weight.

In one embodiment, it is contemplated that more than one biologically active substance is present in the liquid composition.

In one embodiment, if the composition is to be used as bulking agent for soft tissue augmentation, it is contemplated that no biologically active substance is present in the liquid composition.

The biologically active substance may be added, e.g. as a particulate powder or as a solution in a solvent compatible with the aqueous solution of dextran. It may be incorporated into the water before adding dextran so as to give the liquid composition of the invention for use in step (b).

In one embodiment, a process for preparing a composition suitable for the controlled release of a biologically active substance in the body of a mammal is thus provided, comprising the steps of (a) providing a liquid composition comprising at least one biologically active substance and an aqueous solution of dextran having a molecular weight of 1-100 kDa; and (b) bringing the liquid composition to solidify;

wherein water is gradually eliminated from the liquid composition during step (b).

Furthermore, in one embodiment of the invention an article for biomedical application is provided, e.g. a hard pharmaceutical capsule, a hard medical device, e.g. a plate, a screw or a pin or a hard medical prosthesis.

Finally, it should be noted that for the purpose of the present invention, the mammal may be a human or an animal, e.g. a farm animal, e.g. a cow, a pig, a horse, or a sheep, a domestic animal, e.g. a dog or a cat, a laboratory animal, e.g. a rat, a mouse or a rabbit etc.

Further embodiments of the invention are as defined herein below and in the claims.

BRIEF DESCRIPTION OF THE DRAWINGS

Day 1 (D1)—fasting state 180 minutes, Day 3 (D3)—15 IU per os at 30th minute, Day 5 (D5)—food at 30th minute, Day 7 (D7)—30 IU per os at-30th minute and food at 30th minute

Figure 1:
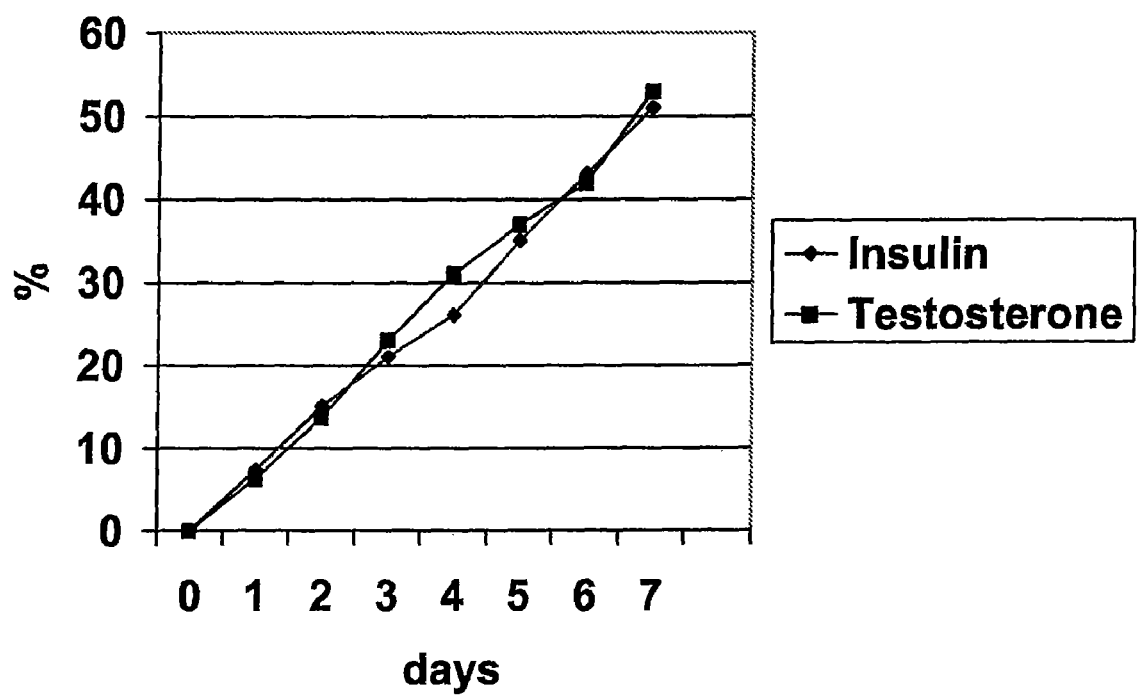
FIG. 1 is a graphic representation of the release of insulin and testosterone under the conditions of Example 4 and Example 5, respectively.

Day 1 (D1)—fasting state 180 minutes, Day 3 (D3)—15 IU per os at 30th minute, Day 5 (D5)—food at 30th minute, Day 7 (D7)—30 IU per os at-30th minute and food at 30th minute

DETAILED DESCRIPTION OF THE INVENTION

The major objects of the invention are to provide polymer matrices for ISFD which are capable of containing the biologically active substances incorporated therein such that the bioactivity of said substance is essentially maintained during the manufacturing process as well as after administration and matrices for capsules aimed to targeted delivery into specific sites of GIT.

Dextran is suitable, perhaps even ideal, matrix material, since it does not need to be dissolved in organic solvents and can degrade into neutral substances, ultimately glucose which is metabolized to water and carbon dioxide and expelled from the body via respiration and urine.

Very advantageously, dextran is a well-known material, and all molecular weight dextrans enzymatically degrade in gastrointestinal tract by enzymes localized in the small-intestinal mucosa and have been reported to be not toxic. (see, e.g., EUROPEAN COMMISSION HEALTH & CONSUMER PROTECTION DIRECTORATE-GENERAL, SCIENTIFIC COMMITTEE ON FOOD CS/NF/DOS/7/ADD 3 "FINAL OPINION OF THE SCIENTIFIC COMMITTEE ON FOOD ON A DEXTRAN PREPARATION, PRODUCED USING LEUCONOSTOC MESENTEROIDES, *SACCHAROMYCES CEREVISIAE* and *LACTOBACILLUS* Spp, AS A NOVEL FOOD INGREDIENT IN BAKERY PRODUCTS" from 18 Oct. 2000). Examples of pharmaceutically acceptable dextrans are those of molecular weight 70 kDa (Macrodex®) and 40 kDa (Rheomacrodex®) which are used intravenously as plasma expanders.

The dextrans of clinical grade are commercially available and have a purity which is acceptable for the manufacture of a parenterally administrable preparation (http://www.dextran.net/buydextran.html). They are able to form sufficiently stable aqueous solutions in sufficiently high concentration to enable a biologically active substance to be admixed under conditions allowing the retention of the bioactivity of such a substance.

Carbohydrate polymers including dextran have a glass transition temperature, which is much higher than that of all synthetic polymers of similar molecular weight. One qualitative picture explaining the high glass transition temperature of amorphous carbohydrates is that, in the dry state, the formation of intermolecular hydrogen bonds between the carbohydrate molecules leads to formation of larger molecular entities, whereas water disrupts the formation of hydrogen bonds between the carbohydrate chains. In accordance with the important role of hydrogen bonding, the formation of the hydrogen bond network proceeds via a complex mechanism involving both hydrogen bond formation and disruption and depends essentially on two parameters—temperature and water activity. Manipulating these parameters, different types of polymer matrices based on carbohydrates may be theoretically obtained owing to quantity of hydrogen bonds formed and their specific spatial distribution.

Several experimental findings made by the inventor have supported his hypothesis that dextran may be used as polymer matrix for oral targeted delivery systems, e.g., capsules, and for ISFDs. The present inventor has shown that highly concentrated aqueous solutions of dextran can be readily obtained. For example, mixing of 2 g of dextran with molecular weight 40 kDa and 1 g of water in a syringe provides a not extremely viscous solution which can be dosed through 18-22 gauge needles. Placed between two surfaces (glass or metal) the dextran solution provides a thin opaque film that is not adhesive to the surfaces mentioned after about eight hours at room temperature. Additional slow drying provides a flexible film which has unique properties. The film can be obtained in the form of cap and body of the standard capsules when glass or metal sticks covered with the solution are used. Dissolution comparative experiments showed that capsules based on dextran matrix and standard gelatin capsules have extremely different rate of dissolution in water, PBS (pH 7.4) and 0.1N HCl. For example, at 37° C. and 1,000 rpm (magnet stirrer) in 50 ml of water, PBS (pH 7.4) or 0.1N HCl, the time of total dissolution was several seconds for gelatin capsule and about 1 h for dextran capsule. However, addition of dextranase in the PBS reduces time of dissolution to several minutes. These experiments, taken together with the mentioned above fact that all molecular weight dextrans enzymatically degrade in gastrointestinal tract by enzymes localized in the small intestine mucosa, give a basis for a new strategy of targeted delivery to small intestine and colon not based on pH sensitive coatings.

It is interesting to note here that there are a lot of scientific publications indicating that dextran can be enzymatically degraded only in colon by bacteria (see, e.g., European Patent Application EP 1 184 032 A1). However, the existence of intestinal dextranase is a well known fact from 1963 (see Dahlqvist A. "Rat Intestinal Dextranase. Localization and relation to the other carbohydrases of the digestive tract", Biochem. J. (1963) 86, 72).

Slow water elimination from highly concentrated aqueous dextran solution after the hydrogen bonds net formation process started is a very important aspect of technology influencing the properties of final product, e.g., capsule shell solubility. Without this water elimination the formation of crystallized dextran particles can occur (especially for low molecular weight dextrans) and integrity of the homogeneous system will be destroyed. The attempts to use crystallized dextran particles for drug delivery are described in literature, for example in the U.S. Pat. No. 4,713,249, European patent application EP 1 184 032 A1, US patent application 20040234615. However, in these publications, there is no suggestion that articles with homogeneous structure, e.g., capsule shell and implants or special devices based on dextran matrix could be obtained.

According to the present invention, however, monolithic implants based on dextran with excellent biocompatibility and mechanical strength may be readily prepared in form of plates, screws and pins to be used for orthopaedic trauma fixation and biodegradable membrane for dental regenerative surgery.

Biodegradable implants in orthopaedics, in contrast to metal implants, do not require a second surgical intervention for removal of the devices, but, they have not been universally adopted, which may be due to the high level of local foreign-body reaction. The process of biodegradation of the most popular prior art implants based on PLA or PGA begins with the polymer chains being broken into smaller fragments by hydrolysis. The molecular weight of the implant decreases first and the mechanical strength of the implant decreases allowing subsequent mechanical fragmentation. Absorption of the implant then occurs through the release of soluble degradation products, phagocytosis by macrophages and intracellular degradation. Tissue responses to fixation implants made of polyglycolide have been reported in more than 15 clinical studies and adverse tissue response rates of up to 47% have been recorded. (Ambrose C G, Clanton T O: Bioabsorbable implants: Review of clinical experience in orthopedic surgery. Annals of Biomedical Engineering 32: 171-177, 2004).

It may be noted that by the term "implant" as used in the present application is meant any foreign object or composition implanted into the body of a mammal, such as a hard medical device, e.g., plate, screw, pin, or a solid or semi-solid foreign body, such as an implant useful for soft tissue augmentation.

It may be added, that the term "biodegradable" means that the ISFD, which is based on dextran, after parenteral administration dissolves in the body and dextran molecules can be excreted through kidneys or ultimately metabolized by organism to water and carbon dioxide.

Water elimination from the concentrated dextran solutions during the process of the homogeneous net of hydrogen bonds formation can be provided by water evaporation or water extraction at an optimal rate, e.g. by the process of water extraction from dextran solution with liquid polyethylene glycol (PEG), polypropylene glycol (PPG), and ethanol. The highly concentrated dextran solutions may be dispersed in the liquid low molecular weight PEG and after solidification close to monolithic dextran microspheres may be obtained. These microspheres may be used as injectable bulking agent, as depot for controlled release, or as oral preparations for targeted delivery.

The active substance mixed with the dextran can be in dissolved form, for example in a buffer solution, or in solid, amorphous or crystalline form, and mixing may be realized at a suitable temperature, which is generally between 0° C. and 45° C., preferably at room temperature (20° C.). It is possible to add the biologically active substance to the dextran solution, or vice versa. Since the biologically active substances suitable for use in this system, for example proteins, are generally macromolecules, it is possible, when mixing a solution of a dissolved macromolecule with dextran, that an emulsion can be formed, in which the macromolecule generally represents the inner phase, or a precipitate. This is entirely acceptable, provided that the biologically active substance retains or does not appreciably lose its bioactivity. Water insoluble substances may be added in form of powder, emulsion or solution in compatible with water solvents, e.g., ethanol. A homogeneous solution, emulsion or suspension is then created by agitation, which can be carried out using a suitable technique well known within the field.

Freeze-drying is often the preferred drying method, since, correctly designed, it is especially mild with respect to the enclosed biologically active substance such as protein. Applied to highly concentrated dextran solutions containing BAS, it provides preparation that can be stored for a long time at room temperature and readily re-hydrated to initial water concentration before application.

The present inventor performed experiments with highly concentrated aqueous solutions of dextran, which are not initially extremely viscous and can be administered by injection into the body of a mammal. These experiments revealed that the dextran solutions may be solidified at physiological conditions in vivo—a fact that has not been previously described in the public area. It has surprisingly been found that when a highly concentrated aqueous dextran solution, e.g., 67% aqueous solution of dextran 40 kDa, is placed in an aqueous medium, e.g. PBS, or injected into a mammal, gel formation occurring during a relatively short time period after exposure to an aqueous environment and release of biologically active substance (BAS) out of the implant formed can be obtained. Furthermore, an extremely important experimental finding is that the release rate of BAS entrapped in implant formed coincides with the rate of the dextran matrix biodegradation (predominantly by dissolution) in the broad range of drugs with different molecular weights and solubility.

The invention is further illustrated by the below examples, which are not to be construed as a limitation for the scope of the invention.

Example 1

Step 1: 1 g of distilled water was mixed with 3 g of dextran (1 kDa, Pharmacosmos) in a 15 ml lab tube to obtain about 75% by weight solution. The mixture was vacuumed at 6 mm Hg to remove air bubbles and centrifuged for 5 min at 2,000 rpm. A clear solution was obtained.

Step 2: Three 15 ml lab tubes containing 1 ml of the dextran solution were prepared and 2 ml of water were added to every tube, which was placed in a shaker at 37° C. and 30 rpm. 1 ml of buffer was taken every 30 min and 1 ml of fresh water was added. The samples of buffer were analyzed gravimetrically for matrix concentration after water evaporation. Close to zero order rate of dissolution during 7 days was revealed and about 50% of matrix mass were dissolved.

Example 2

Step 1: 1 g of PBS pH 7.4 was mixed with 2 g of dextran (40 kDa, Pharmacosmos) in a 15 ml lab tube to obtain about 67% by weight solution. The mixture was vacuumed at 6 mm Hg to remove air bubbles and centrifuged for 5 min at 2,000 rpm, giving a clear solution.

Step 2: Three 15 ml lab tubes containing 1 ml of the solution were prepared and 2 ml of PBS pH 7.4 was added to every tube that was placed in a shaker at 37° C. and 30 rpm. 1 ml of buffer was taken every 30 min and 1 ml of fresh buffer was added. The samples of buffer were analyzed gravimetrically for matrix concentration after water evaporation.

Close to zero order rate of dissolution during 7 days was revealed and about 50% of matrix mass were dissolved.

Example 3

Step 1: 1 g of distilled water was mixed with 2 g of dextran (40 kDa, Pharmacosmos) in a 15 ml lab tube to obtain about 67% by weight solution. The mixture was vacuumed at 6 mm Hg to remove air bubbles and centrifuged for 5 min at 2,000 rpm. A clear solution was obtained.

Step 2: Three 15 ml lab tubes containing 1 ml of the dextran solution were prepared and 2 ml of 0.1N HCl were added to every tube that was placed in a shaker at 37° C. and 30 rpm. 1 ml of medium was taken every 30 min and 1 ml of fresh acid was added. The samples of buffer were analyzed gravimetrically for matrix concentration after water evaporation. Close to zero order rate of dissolution during 7 days was revealed and about 50% of matrix mass were dissolved.

Example 4

Step 1: 1 g of distilled water was mixed with 2 g of dextran (40 kDa, Pharmacosmos) in a 15 ml lab tube to obtain about 67% by weight solution. The mixture was vacuumed at 6 mm Hg to remove air bubbles and centrifuged for 5 min at 2,000 rpm. A clear solution was obtained.

Step 2: 0.1 ml of insulin solution (25 IU) was added to the dextran solution and thoroughly mixed therewith. 2 ml of buffer were added to the tube containing the mixture of dextran and insulin and the tube was placed in a shaker at 37° C. and 30 rpm. 1 ml of buffer was taken every 30 min and 1 ml of fresh buffer was added. The samples of buffer were analyzed for insulin concentration by HPLC and ELISA methods. Close to zero order rate of release of insulin during 7 days was revealed (FIG. 1).

Example 5

Step 1: 1 g of distilled water was mixed with 2 g of dextran (40 kDa, Pharmacosmos) in a 15 ml lab tube to obtain about 67% wt. solution. The mixture was vacuumed at 6 mm Hg to remove air bubbles and centrifuged for 5 min at 2,000 rpm and clear solution was obtained.

Step 2: 0.1 ml of ethanol containing 4 mg of testosterone was added to the dextran solution and thoroughly mixed with. 2 ml of serum was added to the tube containing the mixture of dextran and testosterone and placed in a shaker at 37° C. and 30 rpm. 1 ml of serum was taken every 30 min and 1 ml of fresh one was added. The samples of buffer were analyzed for testosterone by special ELISA method. Zero order release of testosterone during 7 days was revealed (FIG. 1).

The biodegradability and biocompatibility of the ISFD based on dextran have been examined through parenteral injection (subcutaneously and intramuscularly) and histological examination of the tissue as a function of time. Injection is possible through fine calibre needles, e.g. the 22 gauge needles mostly used for intramuscular application. ISFD based on dextran disappeared normally from the mammal's tissue (mice) without any inflammation and connective tissue formation.

Example 6

Step 1: 1 g of distilled water was mixed with 2 g of dextran (40 kDa, Pharmacosmos) in a 15 ml lab tube to obtain about 67% by weight solution. The mixture was vacuumed at 6 mm Hg to remove air bubbles and centrifuged for 5 min at 2,000 rpm and a clear solution was obtained.

Step 2: ISFD formation and its biocompatibility were investigated in vivo by using the mouse as a model. The solution of Step 1 was placed in an insulin syringe and administered as intramuscular and subcutaneous injection into mouse at dose of 20 µl of the solution per animal. Follow-up was 1, 7, 28, and 49 days. Histopathology confirmed ISFD formation which was well tolerated: no inflammatory reaction and connective tissue formation induced by ISFD was revealed after 7 weeks. Because of the rate of implant dissolution in tissue is much lower than in in vitro dissolution tests, experimental results obtained show that the ISFD based on dextran can potentially be used as a controlled release depot system and as a bulking agent for soft tissue augmentation.

Example 7

Step 1: 1.5 ml of insulin Actrapid (Novo Nordisk) was mixed with 3.5 g of dextran (40 kDa, Pharmacosmos) in a 20 ml syringe to obtain about 70% wt. solution.

The solution was dosed in standard hard gelatin capsules #2 (Capsulegel, USA) in dose 0.25 g (7.5 IU) per capsule. The slow water evaporation at room temperature during 12 hours did not influence capsules form and hardness.

Figure 2:
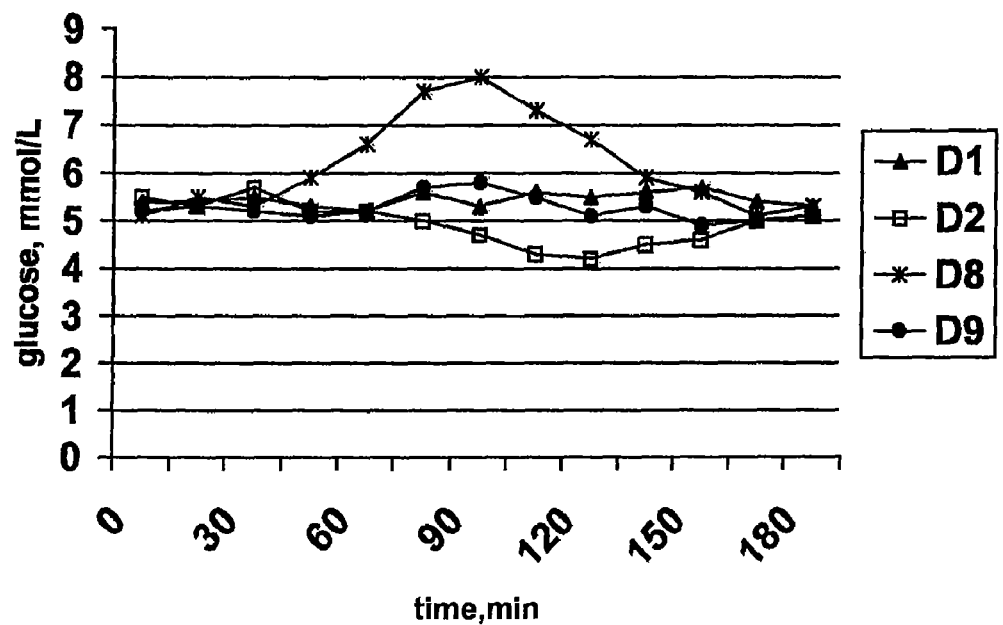
FIG. 2 is a graphic representation of variation of plasma glucose concentrations (mmol/L) in a healthy Subject 1 (BMI 24) as measured after administration of a placebo composition (2 standard gelatin capsules #2 containing 250 mg of dextran 40 kDa each) on day 1 (D1), an insulin-containing composition according to the invention (2 standard gelatin capsules #2 containing 250 mg of dextran matrix and human recombinant insulin 7.5 IU each) on day 2 (D2), and a food composition on day 8 (D8) and insulin-containing composition according to the invention (4 standard gelatin capsules #2 containing 250 mg of dextran matrix and human recombinant insulin 7.5 IU each) on day 9 (D9), respectively.
Figure 3:
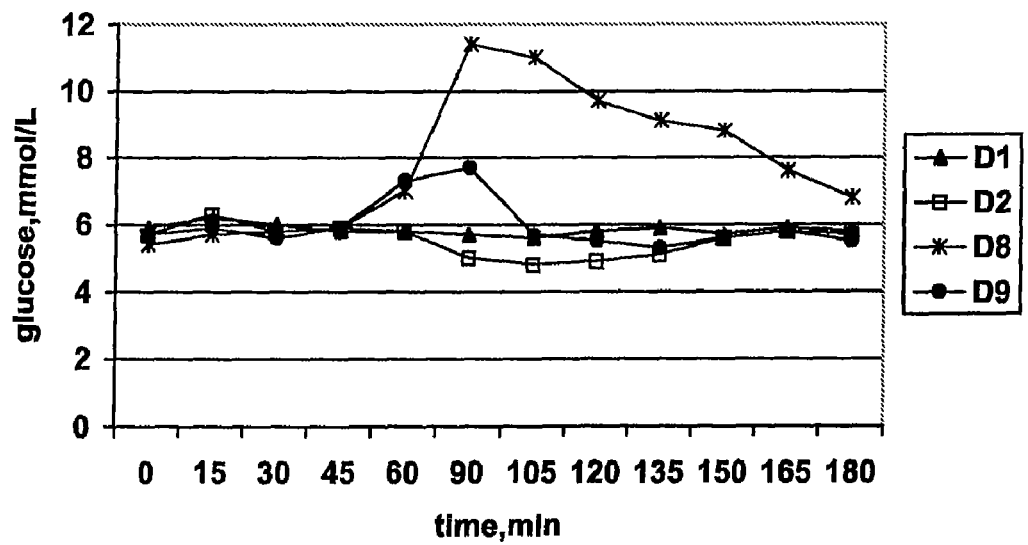
FIG. 3 is a graphic representation of variation of plasma glucose concentrations (mmol/L) in a healthy Subject 2 (BMI 29) as measured after administration of a placebo composition (2 standard gelatin capsules #2 containing 250 mg of dextran 40 kDa each) on day 1 (D1), an insulin-containing composition according to the invention (2 standard gelatin capsules #2 containing 250 mg of dextran matrix and human recombinant insulin 7.5 IU each) on day 2 (D2), and a food composition on day 8 (D8) and insulin-containing composition according to the invention (4 standard gelatin capsules #2 containing 250 mg of dextran matrix and human recombinant insulin 7.5 IU each) on day 9 (D9), respectively.

Step 2: the hypoglycemic effect of the capsules containing insulin was studied in healthy volunteers. Capsules containing 250 mg of dextran 40 kDa (Pharmacosmos) were used as placebo. Experiments were performed on healthy volunteers after an overnight fasting of approximately 12 hours and in the course of experiments blood glucose concentrations were measured (Glucometer One Touch, BASIC Plus, LIFESCAN, Johnson & Johnson). Subjects were without food for 3 hours post dose treatment. Each subject in course of the study received on the first day (Day 1) placebo (standard gelatin capsule containing 250 mg of dextran 40 kDa). At the next day (Day 2), all subjects received two gelatin capsules prepared on Step 1. At 8th day (Day 8) each subject took a carbohydrates reach food and at Day 9th each took the same food and 60 minutes before food four gelatin capsules prepared on Step 1. Blood samples were withdrawn at timed intervals (every 15 min) for the determination of plasma glucose concentrations (mmol/L) (FIGS. 2 and 3).

The experimental data obtained show that the capsules provide valuable hypoglycemic effect in fasting state and effectively decrease maximal sugar levels after eating food.

What is claimed is:

1. A process for preparing a composition, said composition being suitable for the controlled release of a biologically active protein in the body of a mammal, said process comprising:
    (a) providing an aqueous solution of dextran having a molecular weight of 1-100 kDa at a concentration within the range of 25-75% by weight;
    (b) introducing a biologically active protein into the aqueous solution of (a) to form a liquid composition; and
    (c) forming a solid matrix from said dextran in said liquid composition by bringing said dextran in said liquid composition to a solid form by gradually eliminating water from said liquid composition by evaporation or extraction, thereby providing a composition in which said biologically active protein is contained within said solid matrix.

2. The process of claim 1, wherein the molecular weight of dextran is 1-70 kDa.

3. The process of claim 1, wherein dextran is present in said aqueous solution of (a) at a concentration within the range of 50-75% by weight.

4. The process of claim 1, wherein water is eliminated from said liquid composition by evaporation.

5. The process of claim 4, wherein said evaporation is performed at temperature of from 0° C. to 500° C.

6. The process of claim 5, wherein said evaporation is performed at temperature of from 20° C. to 370° C.

7. The process of claim 4, wherein the rate of evaporation is 0.1-75% by weight of said liquid composition per hour.

8. The process of claim 1, wherein water is eliminated from said liquid composition by extraction.

9. The process of claim 8, wherein said extraction is performed by adding 1-10 parts by weight of ethanol, liquid polyethylene glycol (PEG), or liquid polypropylene glycol (PPG), to 1 part by weight of said liquid composition.

10. The process of claim 1, wherein said biologically active protein is dissolved or suspended in said aqueous solution.

11. The process of claim 1, wherein said biologically active protein is introduced in an amount so as to be present at a concentration of 0.01 to 25% by weight in said liquid composition.

12. The process of claim 1, wherein said protein is insulin.

13. An article for biomedical applications comprising a composition prepared by the process of claim 1.

14. The article of claim 13, wherein said article is in the form of a hard pharmaceutical capsule.

15. The article of claim 13, wherein said protein is insulin.

16. The article of claim 13, wherein said protein is insulin and said article is in the form of a hard pharmaceutical capsule.

* * * * *